United States Patent
Angel et al.

(10) Patent No.: US 11,364,198 B2
(45) Date of Patent: Jun. 21, 2022

(54) POLYMERIC EMULSION DELIVERY SYSTEMS

(71) Applicant: BAUSCH HEALTH IRELAND LIMITED, Dublin (IE)

(72) Inventors: Arturo Angel, Santa Rosa, CA (US); Chandelle Hermes, Petaluma, CA (US)

(73) Assignee: BAUSCH HEALTH IRELAND LIMITED, Dublin (IE)

( * ) Notice: Subject to any disclaimer, the term of this patent is extended or adjusted under 35 U.S.C. 154(b) by 74 days.

(21) Appl. No.: 16/377,126

(22) Filed: Apr. 5, 2019

(65) Prior Publication Data

US 2019/0307682 A1    Oct. 10, 2019

Related U.S. Application Data

(60) Provisional application No. 62/653,369, filed on Apr. 5, 2018.

(51) Int. Cl.

| *A61K 9/107* | (2006.01) |
| *A61K 47/32* | (2006.01) |
| *A61K 31/203* | (2006.01) |
| *A61K 31/573* | (2006.01) |
| *A61K 9/00* | (2006.01) |
| *A61K 9/06* | (2006.01) |
| *A61K 31/4436* | (2006.01) |

(52) U.S. Cl.
CPC ............ *A61K 9/107* (2013.01); *A61K 9/0014* (2013.01); *A61K 9/06* (2013.01); *A61K 31/203* (2013.01); *A61K 31/4436* (2013.01); *A61K 31/573* (2013.01); *A61K 47/32* (2013.01)

(58) Field of Classification Search
CPC ........ A61K 9/107; A61K 9/0014; A61K 9/06; A61K 31/203; A61K 31/4436; A61K 31/573; A61K 47/32
USPC ........................................... 514/171
See application file for complete search history.

(56) References Cited

U.S. PATENT DOCUMENTS

| 5,658,575 A | 8/1997 | Ribier et al. |
| 6,585,983 B1 | 7/2003 | Gers-Barlag et al. |
| 8,343,945 B2 | 1/2013 | Tamarkin et al. |
| 8,992,994 B2 | 3/2015 | Roy et al. |
| 9,101,662 B2 | 8/2015 | Tamarkin et al. |
| 9,549,898 B2 | 1/2017 | Tamarkin et al. |
| 10,653,656 B2 * | 5/2020 | Bhatt ................... A61K 9/0014 |
| 2007/0167479 A1 | 7/2007 | Busch et al. |
| 2009/0176749 A1 | 7/2009 | Harada |
| 2012/0289596 A1 | 11/2012 | Rawlings et al. |
| 2013/0095185 A1 | 4/2013 | Toledano et al. |
| 2016/0367570 A1 * | 12/2016 | Dow ..................... A61K 9/107 |

FOREIGN PATENT DOCUMENTS

| EP | 0 793 966 A1 | 9/1997 |
| GB | 2 150 433 A | 7/1985 |
| IT | MI20 110 849 A1 | 11/2012 |
| WO | 91/11187 A1 | 8/1991 |
| WO | 93/17674 A1 | 9/1993 |
| WO | 03/005974 A2 | 1/2003 |
| WO | 2009/129627 A1 | 10/2009 |
| WO | 2016/038553 A1 | 3/2016 |

OTHER PUBLICATIONS

International preliminary reporton patentability PCT/US2019/026185 (Year: 2020).*
International Search Report issued in connection with corresponding International Application No. PCT/US19/26185, dated Jul. 1, 2019, 1 page.
Supplementary European Search Report dated Feb. 23, 2022 in corresponding European Patent Application No. 19782201.8, 15 pages.
Anonymous: "Personal Care—catalog of products 2015", Jan. 1, 2015 (Jan. 1, 2015), pp. 1-98, XP055891124, Retrieved from the Internet: URL:https://www.kemiropa.com.tr/tr/wp-content/uploads/2018/05/PDF-22.pdf [retrieved on Feb. 14, 2022].
Anonymous: "TEGO Carbomer 134, TEGO Carbomer 140, TEGO Carbomer 141", Oct. 1, 2006 (Oct. 1, 2006), pp. 1-4, XP055891332, Retrieved from the Internet: URL:http://glenncorp.com/wp-content/uploads/2013/11/TEGO-Carbomer-134_DS_I1006.pdf [retrieved on Feb. 14, 2022].

* cited by examiner

*Primary Examiner* — Yevgeny Valenrod
(74) *Attorney, Agent, or Firm* — Kilpatrick Townsend & Stockton LLP

(57) ABSTRACT

Provided herein are compositions comprising an oil-in-water emulsion, wherein the emulsion comprises a liquid oil component; a cross-linked homopolymer based on acrylic acid and/or a cross-linked copolymer of acrylic acid and acrylic acid esters; and water. In some embodiments, the composition is a vehicle for the delivery of an active agent.

15 Claims, No Drawings

POLYMERIC EMULSION DELIVERY SYSTEMS

CROSS-REFERENCE TO RELATED APPLICATIONS

This application claims priority to U.S. Provisional Patent Application No. 62/653,369, filed Apr. 5, 2018, the entire contents of which are incorporated by reference herein.

BACKGROUND OF THE INVENTION

Topical administration is a preferred route of administration for local delivery of many active agents. A key aspect of topical administration is designing a delivery system that delivers an optimal concentration of active agent at the site of action for an appropriate duration of time. There remains a need for compositions and vehicles for delivering an active agent.

BRIEF SUMMARY OF THE INVENTION

In one aspect, topical pharmaceutical compositions are provided. In some embodiments, the topical composition comprises:
  a liquid oil component;
  a cross-linked homopolymer based on acrylic acid as a first emulsifier; and water;
  wherein the composition forms a stable oil-in-water emulsion.

In some embodiments, the liquid oil component is present in an amount of about 30% or less by weight of the composition. In some embodiments, the liquid oil component is present in an amount of about 20% or less by weight of the composition. In some embodiments, the liquid oil component comprises mineral oil, light mineral oil, a fatty alcohol, a monocarboxylic acid ester, a dicarboxylic acid ester, a medium chain triglyceride, a long chain triglyceride, or a combination thereof.

In some embodiments, the cross-linked homopolymer is present in an amount of about 0.01-5% by weight of the composition. In some embodiments, the cross-linked homopolymer is present in an amount of about 0.01-3% by weight of the composition. In some embodiments, the cross-linked homopolymer is a carbomer homopolymer type A and/or carbomer homopolymer type C.

In some embodiments, the liquid oil component and the cross-linked homopolymer are present in a ratio in the range of about 1:1 to about 28:1. In some embodiments, the liquid oil component and the cross-linked homopolymer are present in a ratio in the range of about 1:1 to about 20:1. In some embodiments, the liquid oil component and the cross-linked homopolymer are present in a ratio in the range of about 3:1 to about 10:1.

In some embodiments, the composition further comprises a surfactant or a cross-linked copolymer of acrylic acid and acrylic acid esters as a second emulsifier. In some embodiments, the composition comprises a cross-linked copolymer of acrylic acid and acrylic acid esters in an amount of about 0.01-3% by weight of the composition. In some embodiments, the cross-linked copolymer of acrylic acid and acrylic acid esters is a carbomer copolymer type B and/or a carbomer copolymer type A. In some embodiments, the composition comprises a nonionic, anionic, or cationic surfactant in an amount up to about 0.5% by weight of the composition. In some embodiments, the composition comprises a nonionic surfactant selected from the group consisting of sorbitan esters, polyoxyethylene derivatives of a sorbitan ester, glyceryl monostearate, polyoxyethylene monooleate, polyoxyethylene monostearate and polyoxyethylene monolaurate. In some embodiments, the composition comprises an anionic surfactant selected from the group consisting of an alkali soap, an amine soap, and a detergent. In some embodiments, the composition comprises a cationic surfactant selected from the group consisting of quaternium ammonium salts and quaternary amine salts. In some embodiments, the composition does not comprise a second emulsifier.

In some embodiments, the composition further comprises an active agent.

In some embodiments, the oil-in-water emulsion is stable for at least 24 hours at 40° C. In some embodiments, the oil-in-water emulsion is stable for at least 4, 5, 6, 7, 8, 9, 10, 11, 12 weeks or longer at room temperature (22-25° C.). In some embodiments, the oil-in-water emulsion is stable for at least 1, 2, 3, 4, 5, 6, 7, 8, 9, 10, 11, 12 months or longer at room temperature. In some embodiments, the oil-in-water emulsion is stable for at least 1, 2, 3, 4, or 5 years or longer at room temperature.

In another aspect, a topical pharmaceutical composition comprises:
  a liquid oil component, wherein the liquid oil component is in an amount of about 30% or less by weight of the composition;
  a polymer selected from the group consisting of a cross-linked homopolymer based on acrylic acid in an amount of about 0.01-5% by weight of the composition, a cross-linked copolymer of acrylic acid and acrylic acid esters in an amount of about 0.01-5% by weight of the composition, and combinations thereof; and
  water.

In some embodiments, the composition comprises a polymer that is a cross-linked homopolymer based on acrylic acid. In some embodiments, the composition comprises a cross-linked homopolymer based on acrylic acid in an amount of about 0.01-3% by weight of the composition. In some embodiments, the cross-linked homopolymer based on acrylic acid is a carbomer homopolymer type A, a carbomer homopolymer type B, or a carbomer homopolymer type C. In some embodiments, the carbomer homopolymer is a carbomer homopolymer type A.

In some embodiments, the composition comprises a polymer that is a cross-linked copolymer of acrylic acid and acrylic acid esters. In some embodiments, the composition comprises a cross-linked copolymer of acrylic acid and acrylic acid esters in an amount of about 0.01-3% by weight of the composition. In some embodiments, the cross-linked copolymer of acrylic acid and acrylic acid esters is a carbomer copolymer type B and/or a carbomer copolymer type A.

In some embodiments, the polymer is a combination of a cross-linked homopolymer based on acrylic acid and a cross-linked copolymer of acrylic acid and acrylic acid esters. In some embodiments, the polymer is a combination of a carbomer homopolymer type A and a carbomer copolymer type B. In some embodiments, the ratio of the amount of the cross-linked homopolymer based on acrylic acid to that of the cross-linked copolymer of acrylic acid and acrylic acid esters is in the range of 1.6:1 to about 100:1.

In some embodiments, the liquid oil component is present in an amount of about 20% or less by weight of the composition. In some embodiments, the liquid oil component and the polymer are present in a ratio in the range of about 1:1 to about 28:1. In some embodiments, the liquid oil component and the polymer are present in a ratio in the range of about 1:1 to about 20:1. In some embodiments, the liquid oil component and the polymer are present in a ratio in the range of about 3:1 to about 10:1. In some embodiments, the liquid oil component comprises mineral oil, light mineral oil, a fatty alcohol, a monocarboxylic acid ester, a dicarboxylic acid ester, a medium chain triglyceride, a long chain triglyceride, or a combination thereof.

In some embodiments, the composition further comprises an active agent.

In another aspect, kits are provided. In some embodiments, the kit comprises a topical pharmaceutical composition as disclosed herein. In some embodiments, the kit further comprises instructions for use, e.g., according to a method as disclosed herein. In some embodiments, the kit is for use in treating a condition or disorder as disclosed herein, e.g., a skin condition or disorder.

In still another aspect, therapeutic methods comprising the use of a topical pharmaceutical composition as disclosed herein are provided. In some embodiments, the method comprises administering a topical pharmaceutical composition as disclosed herein to a subject in need thereof.

DETAILED DESCRIPTION OF THE INVENTION

I. Introduction

Disclosed herein are pharmaceutical compositions (such as topical compositions) comprising an oil-in-water emulsion, wherein the emulsion comprises a liquid oil component; one or both of a cross-linked homopolymer based on acrylic acid and a cross-linked copolymer of acrylic acid and acrylic acid esters; and water. In some embodiments, the composition is a vehicle for the delivery of an active agent. As detailed herein, it has been discovered that cross-linked polymers based on acrylic acid form emulsions that provide stable conditions where emulsion droplets retain their distribution across time and temperature, active pharmaceutical ingredients retain their chemical integrity even without the presence of stabilizing agents, such as sequestering or antioxidant agents, and dermal and ocular disposition of a given active pharmaceutical ingredient can be enhanced.

Furthermore, as detailed herein, it has been surprisingly discovered that cross-linked homopolymers based on acrylic acid can function as a first emulsifier to form a stable emulsion with an oil component, even in the absence of a surfactant or another polymeric component (i.e., without a second emulsifier). Thus, in another aspect, the present disclosure relates to compositions comprising a liquid oil component, a cross-linked homopolymer based on acrylic acid as a first emulsifier, and water, wherein the amount of the cross-linked homopolymer based on acrylic acid is sufficient to form a stable oil-in-water emulsion in the absence of a surfactant or another polymeric component (e.g., cross-linked copolymer of acrylic acid and acrylic acid esters).

II. Definitions

As used herein, the singular forms "a", "an" and "the" include plural referents unless the content clearly dictates otherwise. The terms "about" and "approximately," when used to modify an amount specified in a numeric value or range, indicate that the numeric value as well as reasonable deviations from the value known to the skilled person in the art, for example, ±20%, ±10%, or ±5%, or ±2.5%, or ±1%, or ±0.5%, are within the intended meaning of the recited value.

As used herein, the term "cross-linked homopolymer based on acrylic acid" refers to a polymer comprising acrylic acid polymer chains that are cross-linked to each other. In some embodiments, the homopolymer is a predominantly high molecular weight cross-linked homopolymer of acrylic acid as described herein.

As used herein, the term "cross-linked copolymer of acrylic acid and acrylic acid esters" refers to a polymer comprising acrylic acid and acrylic acid ester copolymers (e.g., block copolymers) that are cross-linked to each other. In some embodiments, the copolymer is a predominantly high molecular weight cross-linked copolymer of acrylic acid and alkyl acrylate.

As used herein, the term "active agent" refers to a chemical material or compound that induces a desired pharmacological or physiological effect, and include agents that are therapeutically effective, prophylactically effective, or cosmeceutically effective. The term also encompasses pharmaceutically acceptable, pharmacologically active derivatives and analogs of those active agents specifically mentioned herein, including, but not limited to, salts, esters, amides, prodrugs, active metabolites, inclusion complexes, analogs, and the like.

As used herein, the term "therapeutically effective amount" refers to an amount of an agent (e.g., an active agent) that treats, alleviates, abates, or reduces the severity of symptoms of disease in a subject. In some embodiments, a therapeutically effective amount of an agent (e.g., an active agent) diminishes symptoms, makes an injury, disease, or condition (e.g., a skin disorder) more tolerable, slows the rate of degeneration or decline, or improves a patient's physical or mental well-being. The effect of treatment can be compared to an individual or pool of individuals not receiving the treatment, or to the same patient prior to treatment or at a different time during treatment.

The term "administer" refers to a method of delivering agents, compounds, or compositions to the desired site of biological action. These methods include, but are not limited to, topical delivery or ocular delivery. In some embodiments, a composition as disclosed herein is administered topically (e.g., by applying a thin film of a lotion formulation to the affected area, such as the face, back, neck or shoulders of a subject with acne).

The terms "subject," "individual," and "patient," as used interchangeably herein, refer to a mammal, including but not limited to humans, non-human primates, rodents (e.g., rats, mice, and guinea pigs), rabbits, dogs, cows, pigs, horses, and other mammalian species. In some embodiment, a subject, individual, or patient is a human.

III. Compositions

In one aspect, the present disclosure provides compositions such as topical compositions comprising a liquid oil component and one or both of a cross-linked homopolymer based on acrylic acid and a cross-linked copolymer of acrylic acid and acrylic acid esters, wherein the composition is an oil-in-water emulsion. In some embodiments, the composition is a vehicle for the delivery of an active agent. In some embodiments, the composition is formulated as a lotion (e.g., an oil-in-water emulsion or a water-in-oil emulsion). In some embodiments, the composition is formulated as a cream.

Compositions Comprising Polymeric Emulsifiers

Compositions according to the present disclosure generally include a cross-linked homopolymer as the first emulsifier. The first emulsifier can be considered a "primary emulsifier," as it is generally sufficient to form a stable emulsion with an oil component. In some embodiments, the first emulsifier is used in the absence of another emulsifier. In some embodiments, the first emulsifier is used in the presence of one or more other emulsifiers, i.e., in addition to the first emulsifier, the composition contains a second emulsifier, such as a surfactant and/or another polymeric component (e.g., a cross-linked copolymer of acrylic acid and acrylic acid esters).

In some embodiments, a composition (such as a topical composition) comprises:
 a liquid oil component;
 a cross-linked homopolymer based on acrylic acid as a first emulsifier; and
 water;
 wherein the composition forms a stable oil-in-water emulsion.

In some embodiments, a composition (such as a topical composition) comprises an oil-in-water emulsion, wherein the emulsion comprises:
 a liquid oil component;
 a cross-linked homopolymer based on acrylic acid as a first emulsifier; and
 water;
 wherein the amount of the cross-linked homopolymer is sufficient to form a stable oil-in-water emulsion in the absence of a surfactant or a cross-linked copolymer of acrylic acid and acrylic acid esters.

In some embodiments, the cross-linked homopolymer is present in an amount of about 0.01-5% by weight of the composition. In some embodiments, the cross-linked homopolymer is present in an amount of about 0.01-4% by weight of the composition, or in an amount from about 0.01-3% by weight of the composition, or in an amount from about 0.01-2% by weight of the composition, or in an amount from about 0.01-1% by weight of the composition, or in an amount from about 0.05-5% by weight of the composition, or in an amount from about 0.05-2.5% by weight of the composition, or in an amount from about 0.05-1.5% by weight of the composition, or in an amount from about 0.05-1% by weight of the composition. In some embodiments, the cross-linked homopolymer is present in an amount of about 0.01%, or about 0.05%, or about 0.1%, or about 0.2%, or about 0.3%, or about 0.4%, or about 0.5%, or about 0.6%, or about 0.7%, or about 0.8%, or about 0.9%, or about 1%, or about 1.5%, or about 2%, or about 2.5%, or about 3%, or about 3.5%, or about 4%, or about 4.5%, or about 5% by weight of the composition.

In some embodiments, the liquid oil component is present in an amount of about 30%, or less (such as 0.01-30%, 0.1-30%, or 0.1-25%), by weight of the composition. In some embodiments, the liquid oil component is present in an amount of about 20%, or less (such as 0.01-20% or 0.5-20%), by weight of the composition. In some embodiments, the liquid oil component is present in an amount of about 15% or less by weight of the composition, or about 10% or less by weight of the composition, or about 8% or less by weight of the composition. In some embodiments, the liquid oil component is present in an amount of about 1-20% by weight of the composition, or in an amount from about 1% to about 15% by weight of the composition, or in an amount from about 1% to about 10% by weight of the composition, or in an amount from about 1% to about 5% by weight of the composition, or in an amount from about 2% to about 4% by weight of the composition. In some embodiments, the liquid oil component is present in an amount of about 5-20% by weight of the composition, or in an amount of about 5-15% by weight of the composition, or in an amount of about 5-10% by weight of the composition. In some embodiments, the liquid oil component is present in an amount up to about 10% by weight of the composition, e.g., up to about 8%, up to about 7.5%, up to about 7%, up to about 6%, up to about 5%, up to about 4.5%, up to about 4%, up to about 3.5%, up to about 3%, or up to about 2.5%.

In some embodiments, the oil component is present in an amount up to about 5% by weight of the composition, e.g., up to about 4.5%, up to about 4%, up to about 3.5%, up to about 3%, or up to about 2.5%. The amount of the oil component can range from about 1.5% to about 2.5%, or from about 1% to about 3%, or from about 0.5% to about 3.5%, or from about 0.25% to about 4%, or from about 0.1% to about 5%, or from about 0.05% to about 5.5% by weight of the composition. In some embodiments, the oil component is present in an amount ranging from about 2% to about 4% by weight of the composition, e.g., about 2%, about 2.5%, about 3%, about 3.5%, or about 4% by weight of the composition. In some embodiments, the oil component is present in an amount ranging from about 1% to about 5% by weight of the composition. In some embodiments, the oil component is present in an amount ranging from about 1.5% to about 4% by weight of the composition. In some embodiments, the oil component is present in an amount ranging from about 2% to about 4% by weight of the composition. In some embodiments, the oil component is present in an amount ranging from about 1% to about 3% by weight of the composition.

In some embodiments, the ratio of the amount of the liquid oil component to that of the cross-linked homopolymer is in the range of about 1:1 to about 28:1. In some embodiments, the ratio of the amount of the liquid oil component to that of the cross-linked homopolymer is in the range of about 1:1 to about 24:1. In some embodiments, the ratio of the amount of the liquid oil component to that of the cross-linked homopolymer is in the range of about 1:1 to about 20:1. In some embodiments, this ratio is in the range of about 1:1 to about 10:1. In some embodiments, this ratio is in the range of about 2:1 to about 10:1, or in the range of about 3:1 to about 10:1, or in the range of about 2:1 to about 9:1. In some embodiments, this ratio is in the range of no greater than 10:1.

In some embodiments, the oil-in-water emulsion that is formed from the liquid oil component and the cross-linked homopolymer is stable for at least 24 hours at accelerated conditions (e.g., 40° C.). In some embodiments, the oil-in-water emulsion is stable for at least 2, 3, 4, 5, 6, 7 days or longer at accelerated conditions (e.g., 40° C.). In some embodiments, the oil-in-water emulsion is stable for at least 1, 2, 3, 4, 5, 6, 7, 8, 9, 10 weeks or longer at accelerated conditions (e.g., 40° C.). In some embodiments, the oil-in-water emulsion is stable for at least 4, 5, 6, 7, 8, 9, 10, 11, 12 weeks or longer at room temperature (22-25° C.). In some embodiments, the oil-in-water emulsion is stable for at least 1, 2, 3, 4, 5, 6, 7, 8, 9, 10, 11, 12 months or longer at room temperature. In some embodiments, the oil-in-water emulsion is stable for at least 1, 2, 3, 4, or 5 years or longer at room temperature.

In some embodiments, the composition further comprises a surfactant or a cross-linked copolymer of acrylic acid and acrylic acid esters as a second emulsifier. In some embodiments, the composition comprises a cross-linked copolymer of acrylic acid and acrylic acid esters in an amount from about 0.01-3% by weight of the composition, or in an amount from about 0.01-2% by weight of the composition, or in an amount from about 0.01-1% by weight of the composition, or in an amount from about 0.01-0.5% by weight of the composition, or in an amount from about 0.01-0.3% by weight of the composition, or in an amount from about 0.01-0.2% by weight of the composition. In some embodiments, the composition comprises a cross-linked copolymer of acrylic acid and acrylic acid esters in an amount up to about 2% by weight of the composition, or up to about 1% by weight of the composition, or up to about 0.5% by weight of the composition, or up to about 0.3% by weight of the composition, or up to about 0.2% by weight of the composition.

In some embodiments, the composition further comprises a surfactant as a second emulsifier. In some embodiments, the composition comprises a nonionic, anionic, or cationic surfactant in an amount up to about 0.5% by weight of the composition, or up to about 0.4% by weight of the composition, or up to about 0.3% by weight of the composition, or up to about 0.2% by weight of the composition. In some embodiments, the composition comprises a nonionic, anionic, or cationic surfactant in an amount of about 0.01-0.5% by weight of the composition, or in an amount of about 0.01-0.3% by weight of the composition, or in an amount of about 0.01-0.2% by weight of the composition. In some embodiments, the composition comprises a nonionic surfactant selected from the group consisting of sorbitan esters, polyoxyethylene derivatives of a sorbitan ester, glyceryl monostearate, polyoxyethylene monooleate, polyoxyethylene monostearate and polyoxyethylene monolaurate. In some embodiments, the composition comprises an anionic surfactant selected from the group consisting of an alkali soap, an amine soap, and a detergent. In some embodiments, the composition comprises a cationic surfactant selected from the group consisting of quaternium ammonium salts and quaternary amine salts.

In some embodiments, the composition does not comprise a second emulsifier. In some embodiments, the composition does not comprise a cross-linked copolymer of acrylic acid and acrylic acid esters. In some embodiments, the composition does not comprise a surfactant.

In some embodiments, a topical composition comprises an oil-in-water emulsion, wherein the emulsion comprises:
  a liquid oil component, wherein the liquid oil component is in an amount of about 30% or less by weight of the composition;
  a polymer selected from the group consisting of a cross-linked homopolymer based on acrylic acid in an amount of about 0.01-5% by weight of the composition, a cross-linked copolymer of acrylic acid and acrylic acid esters in an amount of about 0.01-5% by weight of the composition, and combinations thereof; and
  water.

In some embodiments, the composition comprises a cross-linked homopolymer based on acrylic acid in an amount of about 0.01-5% by weight of the composition. In some embodiments, the cross-linked homopolymer is present in an amount of about 0.01-4% by weight of the composition, or in an amount from about 0.01-3% by weight of the composition, or in an amount from about 0.01-2% by weight of the composition, or in an amount from about 0.01-1% by weight of the composition, or in an amount from about 0.05-5% by weight of the composition, or in an amount from about 0.05-2.5% by weight of the composition. In some embodiments, the cross-linked homopolymer is present in an amount of about 0.01%, or about 0.05%, or about 0.1%, or about 0.2%, or about 0.3%, or about 0.4%, or about 0.5%, or about 0.6%, or about 0.7%, or about 0.8%, or about 0.9%, or about 1%, or about 1.5%, or about 2%, or about 2.5%, or about 3%, or about 3.5%, or about 4%, or about 4.5%, or about 5% by weight of the composition.

In some embodiments, the composition comprises a cross-linked copolymer of acrylic acid and acrylic acid esters in an amount of about 0.01-5% by weight of the composition. In some embodiments, the cross-linked copolymer is present in an amount of about 0.01-4% by weight of the composition, or in an amount from about 0.01-3% by weight of the composition, or in an amount from about 0.01-2% by weight of the composition, or in an amount from about 0.01-1% by weight of the composition, or in an amount from about 0.05-5% by weight of the composition, or in an amount from about 0.05-2.5% by weight of the composition. In some embodiments, the cross-linked copolymer is present in an amount of about 0.01%, or about 0.05%, or about 0.1%, or about 0.2%, or about 0.3%, or about 0.4%, or about 0.5%, or about 0.6%, or about 0.7%, or about 0.8%, or about 0.9%, or about 1%, or about 1.5%, or about 2%, or about 2.5%, or about 3%, or about 3.5%, or about 4%, or about 4.5%, or about 5% by weight of the composition.

In some embodiments, the composition comprises both a cross-linked homopolymer based on acrylic acid in an amount of about 0.01-5% by weight of the composition and a cross-linked copolymer of acrylic acid and acrylic acid esters in an amount of about 0.01-5% by weight of the composition. In some embodiments, the composition comprises a cross-linked homopolymer in an amount of about 0.01-4% by weight of the composition, or in an amount from about 0.01-3% by weight of the composition, or in an amount from about 0.01-2% by weight of the composition, or in an amount from about 0.01-1% by weight of the composition, or in an amount from about 0.05-5% by weight of the composition, or in an amount from about 0.05-2.5% by weight of the composition, and comprises a cross-linked copolymer in an amount of about 0.01-4% by weight of the composition, or in an amount from about 0.01-3% by weight of the composition, or in an amount from about 0.01-2% by weight of the composition, or in an amount from about 0.01-1% by weight of the composition, or in an amount from about 0.05-5% by weight of the composition, or in an amount from about 0.05-2.5% by weight of the composition, or in an amount from about 0.05-1.5% by weight of the composition, or in an amount from about 0.05-1% by weight of the composition. In some embodiments, the composition comprises a cross-linked homopolymer in an amount of about 0.01%, or about 0.05%, or about 0.1%, or about 0.2%, or about 0.3%, or about 0.4%, or about 0.5%, or about 0.6%, or about 0.7%, or about 0.8%, or about 0.9%, or about 1%, or about 1.5%, or about 2%, or about 2.5%, or about 3%, or about 3.5%, or about 4%, or about 4.5%, or about 5% by weight of the composition, and comprises a cross-linked copolymer in an amount of about 0.01%, or about 0.05%, or about 0.1%, or about 0.2%, or about 0.3%, or about 0.4%, or about 0.5%, or about 0.6%, or about 0.7%, or about 0.8%, or about 0.9%, or about 1%, or about 1.5%, or about 2%, or about 2.5%, or about 3%, or about 3.5%, or about 4%, or about 4.5%, or about 5% by weight of the composition.

In some embodiments, the cross-linked homopolymer based on acrylic acid and the cross-linked copolymer of acrylic acid and acrylic acid esters are present in a ratio in the range of 0.1:1 to about 100:1. In some embodiments, the composition comprises both a cross-linked homopolymer based on acrylic acid and a cross-linked copolymer of acrylic acid and acrylic acid esters, wherein the cross-linked homopolymer and the cross-linked copolymer are present in a ratio of at least 1.6:1 or greater. In some embodiments, the cross-linked homopolymer based on acrylic acid and the cross-linked copolymer of acrylic acid and acrylic acid esters are present in a ratio in the range of 1.6:1 to about 100:1, or in the range of about 2:1 to about 100:1, or in the range of about 5:1 to about 100:1, or in the range of about 10:1 to about 100:1. In some embodiments, the cross-linked homopolymer based on acrylic acid and the cross-linked copolymer of acrylic acid and acrylic acid esters are present in a ratio in the range of about 2:1 to about 50:1, or in the range of about 5:1 to about 50:1, or in the range of about 10:1 to about 50:1. In some embodiments, the cross-linked homopolymer based on acrylic acid and the cross-linked copolymer of acrylic acid and acrylic acid esters are present in a ratio of at least 2:1 or greater, e.g., at least 3:1, at least 4:1, at least 5:1, at least 6:1, at least 7:1, at least 8:1, at least 9:1, or at least 10:1.

In some embodiments, the liquid oil component is present in an amount of about 30%, or less (such as 0.5-30% or 0.5-25%), by weight of the composition. In some embodiments, the liquid oil component is present in an amount of about 20%, or less (such as 0.5-20%), by weight of the composition. In some embodiments, the liquid oil component is present in an amount of about 15% or less by weight of the composition, or about 10% or less by weight of the composition, or about 8% or less by weight of the composition. In some embodiments, the liquid oil component is present in an amount of about 1-20% by weight of the composition, or in an amount from about 1% to about 15% by weight of the composition, or in an amount from about 1% to about 10% by weight of the composition, or in an amount from about 1% to about 5% by weight of the composition, or in an amount from about 2% to about 4% by weight of the composition. In some embodiments, the liquid oil component is present in an amount of about 5-20% by weight of the composition, or in an amount of about 5-15% by weight of the composition, or in an amount of about 5-10% by weight of the composition. In some embodiments, the liquid oil component is present in an amount up to about 10% by weight of the composition, e.g., up to about 8%, up to about 7.5%, up to about 7%, up to about 6%, up to about 5%, up to about 4.5%, up to about 4%, up to about 3.5%, up to about 3%, or up to about 2.5%.

In some embodiments, the oil component is present in an amount up to about 5% by weight of the composition, e.g., up to about 4.5%, up to about 4%, up to about 3.5%, up to about 3%, or up to about 2.5%. The amount of the oil component can range from about 1.5% to about 2.5%, or from about 1% to about 3%, or from about 0.5% to about 3.5%, or from about 0.25% to about 4%, or from about 0.1% to about 5%, or from about 0.05% to about 5.5% by weight of the composition. In some embodiments, the oil component is present in an amount ranging from about 2% to about 4% by weight of the composition, e.g., about 2%, about 2.5%, about 3%, about 3.5%, or about 4% by weight of the composition. In some embodiments, the oil component is present in an amount ranging from about 1% to about 5% by weight of the composition. In some embodiments, the oil component is present in an amount ranging from about 1.5% to about 4% by weight of the composition. In some embodiments, the oil component is present in an amount ranging from about 2% to about 4% by weight of the composition.

In some embodiments, the oil component is present in an amount ranging from about 1% to about 3% by weight of the composition.

In some embodiments, the liquid oil component and the polymer (e.g., the cross-linked homopolymer, the cross-linked copolymer, or the combination of cross-linked homopolymer and cross-linked copolymer) are present in a ratio in the range of about 1:1 to about 28:1. In some embodiments, the liquid oil component and the polymer (e.g., the cross-linked homopolymer, the cross-linked copolymer, or the combination of cross-linked homopolymer and cross-linked copolymer) are present in a ratio in the range of about 1:1 to about 20:1. In some embodiments, the liquid oil component and the polymer (e.g., the cross-linked homopolymer, the cross-linked copolymer, or the combination of cross-linked homopolymer and cross-linked copolymer) are present in a ratio in the range of about 1:1 to about 10:1. In some embodiments, the liquid oil component and the polymer (e.g., the cross-linked homopolymer, the cross-linked copolymer, or the combination of cross-linked homopolymer and cross-linked copolymer) are present in a ratio in the range of about 2:1 to about 10:1, or in the range of about 3:1 to about 10:1, or in the range of about 2:1 to about 9:1. In some embodiments, the liquid oil component and the polymer (e.g., the cross-linked homopolymer, the cross-linked copolymer, or the combination of cross-linked homopolymer and cross-linked copolymer) are present in a ratio in the range of no greater than 10:1.

Polymeric Components

In some embodiments, the polymeric component is a carbomer homopolymer. In some embodiments, the carbomer homopolymer is a carbomer homopolymer type A, carbomer homopolymer type B, or carbomer homopolymer type C. In some embodiments, a cross-linked homopolymer comprises a carbomer homopolymer type A (e.g., a Carbopol® 981, Carbopol® 71G, or Carbopol® 971P carbomer homopolymer). In some embodiments, the polymeric viscosity increasing agent comprises carbomer homopolymer type C (e.g., a Carbopol® 980 carbomer homopolymer). In some embodiments, the carbomer homopolymer is not Carbopol® 974P.

In some embodiments, the polymer is a cross-linked copolymer of acrylic acid and acrylic acid esters. In some embodiments, the cross-linked copolymer comprises a copolymer of acrylic acid and $C_{10}$-$C_{30}$ alkyl acrylate. In some embodiments, the copolymer is cross-linked with allyl pentaerythritol. In some embodiments, the cross-linked copolymer comprises a copolymer of acrylic acid and $C_{10}$-$C_{30}$ alkyl acrylate cross-linked with allyl pentaerythritol. In some embodiments, the cross-linked copolymer is a carbomer copolymer type B (e.g., Pemulen™ TR-1) and/or a carbomer copolymer type A (e.g., Pemulen™ TR-2). In some embodiments, the cross-linked copolymer is a carbomer copolymer type B. suitable cross-linked copolymers are copolymers of acrylic acid and alkylmethacrylate, cross-linked with allyl ethers of pentaerythritol.

In some embodiments, the carbomer hompolymer type A (e.g., Carbopol® 981) exhibits a viscosity ranging from about 4,000 to about 11,000 cPs; 0.5% at pH 7.5. In some embodiments, the carbomer hompolymer type B (e.g., Carbopol® 974P) exhibits a viscosity ranging from about 25,000 to about 45,000 cPs (e.g., 29,400-39,400 cPs); 0.5% at pH 7.5. In some embodiments, the carbomer hompolymer type C (e.g., Carbopol® 980) exhibits a viscosity ranging from 40,000-60,000 cPs; 0.5% at pH 7.5. Viscosity values can be determined according to known methods, including those described in the carbomer homopolymer monograph in USP 29-NF 24, which is incorporated herein by reference in its entirety.

In some embodiments, the carbomer homopolymer type A (e.g., Pemulen™ TR-2), exhibits a viscosity ranging from about 4,500-13,500. In some embodiments, the carbomer hompolymer type B (e.g., Pemulen™ TR-1) exhibits a viscosity ranging from about 10,000 to about 26,500 cPs; 1.0% at pH 7.5. Viscosity values can be determined according to known methods, including those described in the carbomer copolymer monograph in USP 25-NF 20, which is incorporated herein by reference in its entirety.

Polymeric components and their properties are described in the art. See, e.g., *Principles of Polymer Science and Technology in Cosmetics and Personal Care*, James V. Gruber and Des Goddard, eds., 1$^{st}$ ed., CRC Press (1999).

Liquid Oil Component

In some embodiments, the liquid oil component comprises mineral oil, light mineral oil, a fatty alcohol, a monocarboxylic acid ester, a dicarboxylic acid ester, a medium chain triglyceride, a long chain triglyceride, or a combination thereof. In some embodiments, the liquid oil component comprises a dicarboxylic acid ester and/or a monocarboxylic acid ester. In some embodiments, the liquid oil component comprises medium- or long-chain triglycerides. In some embodiments, the liquid oil component comprises mineral oil. In some embodiments, the liquid oil component comprises a dicarboxylic acid ester.

In some embodiments, the dicarboxylic acid ester (DCAE) has the formula $R_1OOC-(CH_2)n-COOR_2$, wherein $R_1$ and $R_2$ are alkyl groups containing between 1 and 4 carbons or aryl groups and may be the same or may be different, and wherein n is straight or branched and is between 1 and 12. Examples of DCAEs containing one or more aryl groups include dibenzyl esters of dicarboxylic acids. A preferred dicarboxylic acid ester is diethyl sebacate, which has the formula $CH_3CH_2OOC-(CH_2)_8-COOCH_2CH_3$. Diethyl sebacate is considered to be typical of the dicarboxylic acid esters disclosed as each of the parameters $R_1$, $R_2$, and n of diethyl sebacate are approximately in the center of the range of each of the specified parameters. Examples of other suitable dicarboxylic acid esters where $R_1=R_2$ include, but are not limited to, dimethyl, diethyl, dipropyl, diisopropyl, dibutyl and diisobutyl esters such as oxalate, malate, succinate, glutarate, adipate, pimelate, suberate, and azalate. Examples of suitable dicarboxylic acid esters where $R_1 \neq R_2$ include, but are not limited to, methyl ethyl, methyl propyl, methyl butyl, methyl isopropyl, ethyl propyl, ethyl butyl, ethyl isopropyl, and propyl butyl esters such as oxalate, malate, succinate, glutarate, adipate, pimelate, suberate, azalate, and sebacate. In some embodiments, the liquid oil component comprises a dicarboxylic acid ester selected from the group consisting of diethyl sebacate, diisopropyl adipate, and dibutyl sebacate. In some embodiments, the liquid oil component comprises diethyl sebacate. In some embodiments, the liquid oil component comprises a DCAE (e.g., diethyl sebacate) and further comprises mineral oil or light mineral oil.

In some embodiments, the liquid oil component comprises a monocarboxylic acid ester. In some embodiments, the monocarboxylic acid ester (MCAE) is a straight or branched alkyl MCAE, wherein the alkyl group has up to 12 carbon atoms. In some embodiments, the MCAE has the formula $CH_3-(CH_2)_n-COOR_1$, wherein $R_1$, is an alkyl group containing between 1 and 4 carbons or an aryl group, and wherein n is between 1 and 12. Examples of such monocarboxylic acid esters include, but are not limited to, methyl, ethyl, propyl, isopropyl, butyl, or an aryl such as benzyl formate, acetate, propionate, butyrate, valerate, laurate, myristate, palmitate, and stearate. Examples of preferred monocarboxylic acid esters include, but are not limited to, isopropyl palmitate and isopropyl myristate. In some embodiments, the liquid oil component comprises a monocarboxylic acid ester selected from the group consisting of isopropyl myristate, isopropyl palmitate, and benzyl benzoate. In some embodiments, the liquid oil component comprises isopropyl myristate. In some embodiments, the liquid oil component comprises an MCAE (e.g., isopropyl myristate) and further comprises mineral oil or light mineral oil.

In some embodiments, the liquid oil component is present in an amount of about 30%, or less (such as 0.5-30%), by weight of the composition. In some embodiments, the liquid oil component is present in an amount of about 20%, or less (such as 0.5-20%), by weight of the composition. In some embodiments, the liquid oil component is present in an amount up to about 15% by weight of the composition. In some embodiments, the liquid oil component is present in an amount up to about 10% by weight of the composition. In some embodiments, the liquid oil component is present in an amount up to about 7.5% by weight of the composition. In some embodiments, the liquid oil component is present in an amount up to about 5% by weight of the composition, e.g., up to about 4.5%, up to about 4%, up to about 3.5%, up to about 3%, or up to about 2.5%. In some embodiments, the liquid oil component is present in an amount from about 1% to about 15% by weight of the composition. In some embodiments, the liquid oil component is present in an amount from about 1% to about 10% by weight of the composition. In some embodiments, the liquid oil component is present in an amount from about 1% to about 5% by weight of the composition. In some embodiments, the liquid oil component is present in an amount from about 1.5% to about 4% by weight of the composition. In some embodiments, the liquid oil component is present in an amount from about 2% to about 4% by weight of the composition.

In some embodiments, the oil component is present in an amount up to about 5% by weight of the composition, e.g., up to about 4.5%, up to about 4%, up to about 3.5%, up to about 3%, or up to about 2.5%. The amount of the oil component can range from about 1.5% to about 2.5%, or from about 1% to about 3%, or from about 0.5% to about 3.5%, or from about 0.25% to about 4%, or from about 0.1% to about 5%, or from about 0.05% to about 5.5% by weight of the composition. In some embodiments, the oil component is present in an amount ranging from about 2% to about 4% by weight of the composition, e.g., about 2%, about 2.5%, about 3%, about 3.5%, or about 4% by weight of the composition. In some embodiments, the oil component is present in an amount ranging from about 1% to about 5% by weight of the composition. In some embodiments, the oil component is present in an amount ranging from about 1.5% to about 4% by weight of the composition. In some embodiments, the oil component is present in an amount ranging from about 2% to about 4% by weight of the composition. In some embodiments, the oil component is present in an amount ranging from about 1% to about 3% by weight of the composition.

In some embodiments, the liquid oil component and the polymer (e.g., a polymeric viscosity-increasing agent when used as a first emulsifier, or a combination of a polymeric viscosity-increasing agent and a polymeric emulsifier) are present in a ratio in the range of about 1:1 to about 20:1, or from about 1.5:1 to about 20:1, or from about 2:1 to about 15:1, or from about 2:1 to about 10:1, or from about 2:1 to about 7.5:1, or from about 2:1 to about 5:1, or from about 2:1 to about 3:1.

Aqueous Component

In some embodiments, the pharmaceutical composition comprises water, e.g., purified water. In general, the composition comprises water in an amount such that the percentage of water and the percentages of the other components in the composition total 100% (i.e., water is added quantum sufficit). In some embodiments, the composition comprises at least 50% water by weight of the composition, e.g., at least 60%, at least 65%, at least 70%, at least 75%, at least 80%, at least 85%, or at least 90% water by weight of the composition.

Active Agents

In some embodiments, the compositions (e.g., topical compositions) disclosed herein comprise one or more active agents. In some embodiments, the active agent is any compound that is suitable for topical, transdermal or transmucosal delivery and induces a desired local or systemic effect. In some embodiments, the active agent is an agent that is useful for treating a skin condition or disorder. In some embodiments, the composition comprises a cosmeceutically active agent, e.g., a nontoxic agent having a medicinal or drug-like properties which, when applied to the surface of skin, beneficially affects the biological functioning of that skin. In some embodiments, the active agent is a retinoid, a corticosteroid, an antibiotic, an anti-inflammatory agent, or an anti-fungal agent. In some embodiments, the composition comprises two or more active agents. In some embodiments, the composition comprises one, two, or three active agents. In some embodiments, wherein the composition comprises two or more active agents, the active agents are in the same class of agent (e.g., the active agents are both retinoids). In some embodiments, wherein the composition comprises two or more active agents, the active agents are in different classes of agents (e.g., a retinoid and an antibiotic).

In some embodiments, the composition comprises a retinoid. Examples of retinoids include, but are not limited to, retinol, retinal, tretinoin, isotretinoin, alitretinoin, etretinate, acitretin, adapalene, bexarotene, and tazarotene.

In some embodiments, the composition comprises a corticosteroid. Corticosteroids are categorized into seven classes according to their potency as determined based on their vasoconstrictive activity (e.g., as measured in a Vaso-Constrictor Assay). In some embodiments, the corticosteroid is a Class 1 corticosteroid ("Superpotent Corticosteroid"), a Class 2 corticosteroid ("Potent Corticosteroid"), or a Class 3 corticosteroid ("Upper Mid-Strength Corticosteroid"). Examples of corticosteroids include, but are not limited to, clobetasol, halobetasol, betamethasone, fluocinonide, diflorasone, desoximetasone, mometasone, flurandrenolide, halcinonide, amcinonide, budesonide, desonide, beclomethasone, triamcinolone, fluticasone, hydrocortisone, or fluocinolone.

In some embodiments, the composition comprises an antibiotic. Examples of antibiotics include, but are not limited to, clindamycin, erythromycin, natamycin, neomycin, mupirocin, fusidic acid, minocycline, dapsone, and tetracycline.

In some embodiments, the composition comprises an anti-inflammatory agent. In some embodiments, the anti-inflammatory agent is an imidazole compound that suppresses a topical inflammatory response, such as but not limited to metronidazole. In some embodiments, the anti-inflammatory agent is a nonsteroidal anti-inflammatory agent (NSAID). Examples of topical NSAIDs include, but are not limited to, ibuprofen, indomethacin, diclofenac, and naproxen.

In some embodiments, the composition comprises an anti-fungal agent. Examples of anti-fungal agents include, but are not limited to, fluconazole, itraconazole, ketoconazole, amphotericin, nystatin, pimaricin, naftifine, terbinafine, amorolfine, and 5-fluorocytosine.

In some embodiments, the active agent is present in the composition in an amount from about 0.0001% to about 10% by weight of the composition, e.g., in an amount from about 0.01% to about 1%, from about 0.01% to about 0.5%, from about 0.05% to about 1%, from about 0.05% to about 0.5%, from about 0.1% to about 1%, from about 0.1% to about 0.75%, or from about 0.1% to about 0.5%.

Additional Components

In some embodiments, the pharmaceutical composition (e.g., the topical pharmaceutical composition) further comprises one or more additional components. For example, in some embodiments, the pharmaceutical composition comprises one or more humectants, moisturizing agents, antioxidants, preservatives, wetting agents, and/or neutralizing agents.

In some embodiments, the pharmaceutical composition comprises one or more moisturizing agents. Examples of suitable moisturizing agents include, but are not limited to, collagen, elastin, keratin, sodium hyaluronate, cholesterol, squalene, petrolatum, fatty acids, and fatty alcohols. In some embodiments, the moisturizing agent is a non-occlusive (e.g., non-oil) moisturizer. In some embodiments, the pharmaceutical composition comprises soluble collagen and sodium hyaluronate as moisturizing agents. In some embodiments, the one or more moisturizing agents are present in an amount from about 5% to about 20% by weight of the composition, e.g., from about 5% to about 15%, or from about 5% to about 10% by weight of the composition.

In some embodiments, the pharmaceutical composition comprises one or more humectants. Examples of suitable humectants include, but are not limited to, glycerin, sorbitol, xylitol, urea, ethylene glycol, hexylene glycol, polyethylene glycol, and propylene glycol. In some embodiments, the pharmaceutical composition comprises glycerin as a humectant. In some embodiments, the one or more humectants are present in an amount from about 5% to about 20% by weight of the composition, e.g., from about 5% to about 15%, from about 7% to about 15%, or from about 7% to about 10% by weight of the composition.

In some embodiments, the pharmaceutical composition comprises one or more preservatives. Examples of suitable preservatives include, but are not limited to, methyl paraben, ethyl paraben, propyl paraben, butyl paraben, benzyl alcohol, benzoic acid, sorbic acid, and quaternary ammonium compounds. In some embodiments, the pharmaceutical composition comprises methyl paraben, propyl paraben, benzyl alcohol, or a combination thereof as the preservative (s). In some embodiments, the one or more preservatives are present in an amount from about 0.25% to about 5% by weight of the composition, e.g., from about 0.5% to about 3%, from about 0.5% to about 1.5%, or from about 0.25% to about 1% by weight of the composition.

In some embodiments, the pharmaceutical composition comprises one or more antioxidants. Examples of suitable antioxidants include, but are not limited to, alpha-tocopherol, ascorbic acid, butylhydoxyanisole (BHA), butylated hydoxytoluene (BHT), monothioglycerol, potassium metabisulfite, sodium ascorbate, sodium bisulfite, sodium metabisulfite, and sodium sulfite. In some embodiments, the pharmaceutical composition comprises BHT as an antioxidant. In some embodiments, the one or more antioxidants are present in an amount from about 0.1% to about 2% by weight of the composition, e.g., from about 0.15% to about 1%, from about 0.2% to about 1%, or from about 0.2% to about 0.6% by weight of the composition.

In some embodiments, the pharmaceutical composition comprises a surfactant, such as a nonionic surfactant, an anionic surfactant, or a cationic surfactant. In some embodiments, the surfactant functions as a second emulsifier. In some embodiments, the surfactant functions as a wetting agent. In some embodiments, the composition comprises a nonionic, anionic, or cationic surfactant in an amount up to about 0.5% by weight of the composition, or up to about 0.4% by weight of the composition, or up to about 0.3% by weight of the composition, or up to about 0.2% by weight of the composition. In some embodiments, the composition comprises a nonionic, anionic, or cationic surfactant in an amount from about 0.05% to about 0.5% by weight of the composition, or from about 0.1% to about 0.5% by weight of the composition, or from about 0.05% to about 0.4% by weight of the composition, or from about 0.1% to about 0.4% by weight of the composition, or from about 0.1% to about 0.3% by weight of the composition. In some embodiments, the composition comprises a nonionic surfactant selected from the group consisting of sorbitan esters (e.g., sorbitan monolaurate, sorbitan monooleate, sorbitan monopalmitate, sorbitan monostearate, and sorbitan trioleate), polyoxyethylene derivatives of a sorbitan ester (e.g., polysorbate 20, polysorbate 40, polysorbate 60, and polysorbate 80), glyceryl monostearate, polyoxyethylene monooleate, polyoxyethylene monostearate and polyoxyethylene monolaurate. In some embodiments, the composition comprises an anionic surfactant selected from the group consisting of an alkali soap, an amine soap, and a detergent. In some embodiments, the composition comprises a cationic surfactant selected from the group consisting of quaternium ammonium salts and quaternary amine salts.

In some embodiments, the pharmaceutical composition does not comprise a non-ionic surfactant. In some embodiments, the pharmaceutical composition does not comprise an anionic surfactant. In some embodiments, the pharmaceutical composition does not comprise a cationic surfactant.

In some embodiments, the pharmaceutical composition comprises a pH neutralizing agent. In some embodiments, the pH neutralizing agent maintains the pH of the pharmaceutical composition at a pH from about 5-6. Suitable pH neutralizing agents include, but are not limited to, trolamine (triethanolamine), sodium hydroxide, and potassium hydroxide. In some embodiments, the pharmaceutical composition comprises trolamine as a pH neutralizing agent.

Emulsion Stability

In some embodiments, the pharmaceutical compositions disclosed herein form a stable emulsion. In some embodiments, the pharmaceutical compositions disclosed herein form an emulsion (e.g., an oil-in-water emulsion) that remains stable for a prolonged period of time and/or under accelerated conditions. Various methods for measuring emulsion stability are known in the art. In some embodiments, emulsion stability is measured by centrifugation. In some embodiments, emulsion stability is measured by centrifugation under conditions of a centrifugal force of 5000 g for at least 30 minutes. Any of a number of additional emulsion properties can be evaluated during stability testing, such as pH, viscosity, flow behavior, tack/texture, color, odor, specific gravity, phase separation, conductivity, droplet size distribution, preservation, vibration, and or activity of the active agent (e.g., using a chemical or biological assay). In some embodiments, emulsion stability is measured as disclosed in the Examples section below. In some embodiments, phase separation is measured.

In some embodiments, the composition forms an emulsion that is stable under ambient temperature for a prolonged period of time. For example, in some embodiments, the emulsion is stable at 25° C. for at least 1 month, at least 2 months, at least 3 months, at least 4 months, at least 5 months, at least 6 months, at least 7 months, at least 8 months, at least 9 months, at least 10 months, at least 11 months, or at least 12 months or longer. In some embodiments, the emulsion is stable at 25° C. for at least 1 year. In some embodiments, the emulsion is stable at 25° C. for at least 2 years.

In some embodiments, the composition forms an emulsion that is stable under accelerated conditions, such as elevated temperature (e.g., at 37° C., at 40° C., or at 45° C.). In some embodiments, the emulsion is stable for at least 24 hours at 40° C., or is stable for at least 2 days at 40° C., or is stable for at least 3 days at 40° C., or is stable for at least 4 days at 40° C., or is stable for at least 5 days at 40° C., or is stable for at least 6 days at 40° C., or is stable for at least 7 days at 40° C. In some embodiments, the emulsion is stable for 1, 2, 3, 4 weeks or longer under accelerated conditions, e.g., the emulsion is stable for at least 1 week at 40° C., or is stable for at least 2 weeks at 40° C., or is stable for at least 3 weeks at 40° C., or is stable for at least 4 weeks at 40° C., or is stable for at least 1 month at 40° C., or is stable for at least 2 months at 40° C., or is stable for at least 3 months at 40° C., or longer.

IV. Methods of Treatment

In another aspect, therapeutic methods comprising the use of a pharmaceutical composition as disclosed herein are provided. In some embodiments, a pharmaceutical composition as disclosed herein is used for the treatment of a skin condition or disorder. In some embodiments, the skin condition or disorder is acne (e.g., acne vulgaris); psoriasis (e.g., plaque psoriasis, guttate psoriasis, inverse psoriasis, pustular psoriasis, erythrodermic psoriasis, nail psoriasis, or psoriatic arthritis); dermatitis such as atopic, contact, or hand dermatitis, eczema, seborrheic dermatitis, rash, or poison ivy dermatitis; rosacea; or skin lesions. In some embodiments, a pharmaceutical composition as disclosed herein is used cosmetically, e.g., for reducing the appearance of fine lines, wrinkles, fine wrinkling, blotches, hyperpigmentation, skin roughness, or for the improvement of skin tone.

In some embodiments, a pharmaceutical composition as disclosed herein (e.g., a topical pharmaceutical composition comprising an active agent as disclosed in Section III above) is administered to a subject in need thereof for at least 1, 2, 3, 4, 5, 6, or 7 days or longer, e.g., for at least 1, 2, 3, 4, 5, 6, 7, 8, 9, or 10 weeks or longer. In some embodiments, a pharmaceutical composition as disclosed herein is administered to a subject in need thereof for a period of 1-30 days, e.g., 7-30 days, 7-28 days, 7-21 days, 7-14 days, 10-30 days, 14-30 days, or 14-28 days. In some embodiments, a pharmaceutical composition as disclosed herein is administered to a subject in need thereof for a period of 1-30 weeks, e.g., 1-20, 1-10, 1-8, 2-20, 2-15, 2-12, 2-10, 2-8, 4-30, 4-20, 4-12, 4-8, 6-30, 6-20, 6-12, 8-30, 8-24, 8-12, 10-30, 10-20, or 15-30 weeks.

In some embodiments, a pharmaceutical composition as disclosed herein is administered to a subject in need thereof for a period of treatment longer than 2 weeks, longer than 3 weeks, longer than 4 weeks, longer than 1 month, longer than 2 months, longer than 3 months, longer than 4 months, longer than 5 months, or longer than 6 months. In some embodiments, a pharmaceutical composition as disclosed herein is administered to a subject in need thereof for a period of treatment up to 2 weeks, up to 3 weeks, up to 4 weeks, up to 1 month, up to 2 months, up to 3 months, up to 4 months, up to 5 months, or up to 6 months. In some embodiments, a pharmaceutical composition as disclosed herein until improvement or clearance of the disorder or condition (e.g., a skin disorder or condition, such as acne, psoriasis, dermatitis, rash, etc.) is achieved. In some embodiments, the pharmaceutical composition is applied to the affected area or areas one, two, or three times a day. In some embodiments, the pharmaceutical composition is applied to the affected area or areas once daily. In some embodiments, the pharmaceutical composition is applied to the affected area twice daily. In some embodiments, the pharmaceutical composition is applied to the affected area or areas up to two, three, or four times a day.

In some embodiments, a pharmaceutical composition as disclosed herein is administered to a subject in need thereof in two or more treatment periods, in which the treatment periods are separated by a period of time in which the pharmaceutical composition is not administered. For example, in some embodiments, a first treatment period is administered for a period of 1, 2, 3, 4, 5, 6, or 7 days or longer, e.g., least 1, 2, 3, 4, 5, 6, 7, 8, 9, or 10 weeks or longer, then treatment is stopped for at least 1, 2, 3, 4, 5, 6, or 7 days or longer (e.g., for at least 1, 2, 3, 4, 5 weeks or longer) before the second treatment period (e.g., a period of 1, 2, 3, 4, 5, 6, or 7 days or longer, e.g., least 1, 2, 3, 4, 5, 6, 7, 8, 9, or 10 weeks or longer) is administered.

In some embodiments, a pharmaceutical composition as disclosed herein is administered to an adult subject. In some embodiments, a pharmaceutical composition as disclosed herein is administered to a juvenile subject.

V. Kits

In another aspect, kits comprising a pharmaceutical composition (e.g., a topical pharmaceutical composition) as disclosed herein are provided. In some embodiments, the kit comprises a composition comprising:
a liquid oil component;
a cross-linked homopolymer based on acrylic acid as a first emulsifier; and
water;
wherein the composition forms a stable oil-in-water emulsion.
In some embodiments, the kit comprises a composition comprises:
a liquid oil component, wherein the liquid oil component is in an amount of about 30% or less by weight of the composition;
a polymer selected from the group consisting of a cross-linked homopolymer based on acrylic acid in an amount of about 0.01-5% by weight of the composition, a cross-linked copolymer of acrylic acid and acrylic acid esters in an amount of about 0.01-5% by weight of the composition, and combinations thereof; and
water.

In some embodiments, the composition further comprises an active agent. In some embodiments, the active agent is an active agent disclosed in Section III above. In some embodiments, the active agent is an agent that is useful for treating a skin condition or disorder. In some embodiments, the active agent is a retinoid, a corticosteroid, an antibiotic, an anti-inflammatory agent, or an anti-fungal agent.

In some embodiments, the kit comprises a pharmaceutical composition for use in the treatment of a skin condition or disorder. In some embodiments, the kit is for use in the treatment of a skin condition or disorder that is acne (e.g., acne vulgaris); psoriasis (e.g., plaque psoriasis, guttate psoriasis, inverse psoriasis, pustular psoriasis, erythrodermic psoriasis, nail psoriasis, or psoriatic arthritis); dermatitis such as atopic, contact, or hand dermatitis, eczema, seborrheic dermatitis, rash, or poison ivy dermatitis; rosacea; or skin lesions. In some embodiments, the kit is for use in the treatment of acne, e.g., acne vulgaris.

In some embodiments, the kit is for cosmetic use, e.g., for reducing the appearance of fine lines, wrinkles, fine wrinkling, blotches, hyperpigmentation, skin roughness, or for the improvement of skin tone.

In some embodiments, the kit further comprises a product insert and/or instructions for administering the pharmaceutical composition, e.g., according to the methods disclosed herein. While instructional materials typically comprise written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips, USB drives, and SD cards), optical media (e.g., CD-ROM and DVDs) and the like. Such media may include addresses to internet sites that provide such instructional materials.

In some embodiments, the kit further comprises one or more other agents for use in the treatment of the skin disorder or condition. In some embodiments, the pharmaceutical composition as disclosed herein and the one or more other agents can be administered concurrently or sequentially.

VI. Examples

The following examples are offered to illustrate, but not to limit, the claimed invention.

Example 1

Formulation of Emulsion Compositions

Oil-in-water emulsion compositions are prepared as presented in Table 1 below.

TABLE 1

| | % w/w | | | | | | | | | | | | | |
|---|---|---|---|---|---|---|---|---|---|---|---|---|---|---|
| Ingredients | 1 | 2 | 3 | 4 | 5 | 6 | 7 | 8 | 9 | 10 | 11 | 12 | 13 | 14 |
| Diethyl Sebacate | 1.5 | 1.5 | 1.5 | 1.5 | 0.0 | 0.0 | 0.0 | — | — | — | — | — | — | — |
| Light Mineral Oil, NF | 1.5 | 1.5 | 1.5 | 1.5 | 3.0 | 10.0 | 1.0 | 10.0 | 10.0 | — | — | — | — | — |
| Medium Chain Triglycerides | — | — | — | — | — | — | — | — | — | 3.0 | 10.0 | 3.0 | 10.0 | 3.0 |

TABLE 1-continued

| Ingredients | % w/w | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Carbomer Homopolymer Type A (Carbopol 981), NF | 0.8 | 0.9 | 0.95 | 1.0 | 1.0 | 1.0 | 1.0 | 0.95 | 0.9 | 0.95 | 0.95 | 1.0 | 0.95 | — |
| Carbomer Copolymer Type B (Pemulen TR-1), NF | 0.2 | 0.1 | 0.05 | 0.0 | 0.0 | 0.0 | 0.0 | 0.05 | 0.1 | 0.05 | 0.05 | — | 0.05 | — |
| Carbomer Homopolymer Type C (Carbopol 980), NF | — | — | — | — | — | — | — | — | — | — | — | — | — | 1.0 |
| Benzyl Alcohol, NF | 0.9 | | | | | | | | | | | | | |
| Sodium Hydroxide, USP | q.s. pH 5.5 ± 0.3 | | | | | | | | | | | | | |
| Purified Water, USP | Qsad 100 | | | | | | | | | | | | | |

Example 2

Formulation and Testing of Emulsion Compositions

Compositions that were generated and evaluated for efficiency of polyacrylic polymers in emulsifying a system in which its oil phase consisted of liquid oils that made up 11% of the total formula. The components of each composition (Formulation A-D) are presented in Table 2.

TABLE 2

| | Formulation | | | |
|---|---|---|---|---|
| | A | B | C | D |
| Ingredients | % w/w | | | |
| Halobetasol Propionate | 0.01 | 0.01 | 0.01 | 0.01 |
| Tazarotene | 0.045 | 0.045 | 0.045 | 0.045 |
| Diethyl sebacate, NF | 2.97 | 2.97 | 2.97 | 2.97 |
| Light mineral oil, NF | 8.03 | 8.03 | 8.03 | 8.03 |
| Sorbitol solution, 70%, USP | 10.7 | 10.7 | 10.7 | 10.7 |
| Methylparaben, NF | 0.17 | 0.17 | 0.17 | 0.17 |
| Propylparaben, NF | 0.03 | 0.03 | 0.03 | 0.03 |
| Disodium edatate dehydrate, USP | 0.05 | 0.05 | 0.05 | 0.05 |
| Sorbitan monooleate, NF | 0.10 | 0.10 | 0.10 | — |
| Pemulen TR-1 (Carbomer copolymer type B) | 0.40 | — | 0.40 | — |
| Carbopol 981 (Carbomer homopolymer type A) | 0.60 | 0.60 | — | 0.60 |
| Sodium hydroxide | q.s. pH to ~5.0 | | | |
| Purified water | q.s to 100 | | | |

Formulations B and D were prepared using a carbomer homopolymer type A as the sole emulsifier. For Formulations A and C, the ratio of liquid oil component to polymers (carbomer copolymer type B and carbomer homopolymer type A) is 11:1. For Formulations B and D, the ratio of liquid oil component to polymer (carbomer homopolymer type A) is about 18:1.

The stability of Formulations A, B, C, and D were evaluated. Each of Formulations A-D remained physically stable after being stored at 40° C. for a period of at least 3 months.

Example 3

Formulation of Emulsion Compositions

Oil-in-water emulsion compositions were prepared and evaluated for emulsion stability. Emulsion stability was determined by visually evaluating the integrity of the emulsion and confirming the absence of phase separation. The components of each composition (Formulations 1-16) are presented below in Table 3. With the exception of Formulation 13, each of the formulations disclosed in Table 3 remained their integrity after being stored at 50° C. for a period of 9 days.

TABLE 3

| Ingredients | % w/w | | | | | | | | |
|---|---|---|---|---|---|---|---|---|---|
| (% w/w) | 1 | 2 | 3 | 4 | 5 | 6 | 7 | 8 | 9 |
| Diethyl Sebacate | 1.5 | 1.5 | 1.5 | 1.5 | 1.5 | 1.5 | 1.0 | — | — |
| Light Mineral Oil, NF | 1.5 | 1.5 | 1.5 | 1.5 | 1.5 | 1.5 | — | 14.0 | — |
| Medium Chain Triglycerides | — | — | — | — | — | — | — | — | 3.0 |
| Carbomer Homopolymer Type A (Carbopol 981), NF | 0.8 | 0.9 | 0.93 | 0.2 | 0.1 | 0.07 | 0.8 | 0.8 | 0.8 |
| Carbomer Copolymer Type B (Pemulen TR-1), NF | 0.2 | 0.1 | 0.07 | 0.8 | 0.9 | 0.93 | 0.2 | 0.2 | 0.2 |
| Carbomer Homopolymer Type B (Carbopol 974P), NF | — | — | — | — | — | — | — | — | — |

TABLE 3-continued

| Ingredient | | | | | | | | | |
|---|---|---|---|---|---|---|---|---|---|
| Carbomer Homopolymer Type C (Carbopol 980), NF | — | — | — | — | — | — | — | — | — |
| Benzyl Alcohol, NF | | | | 0.9 | | | | | |
| Sodium Hydroxide, USP | | | | q.s. pH 5.5 ± 0.3 | | | | | |
| Trolamine, NF | — | — | — | — | — | — | — | — | — |
| Purified Water, USP | | | | Qsad 100 | | | | | |
| Initial Evaluation | Stable | Stable | Stable | Stable | Stable | Stable | Stable | Stable | Stable |

| Ingredients | % w/w | | | | | | |
|---|---|---|---|---|---|---|---|
| (% w/w) | 10 | 11 | 12 | 13 | 14 | 15 | 16 |
| Diethyl Sebacate | — | — | — | — | — | — | 1.5 |
| Light Mineral Oil, NF | — | — | — | — | — | — | 1.5 |
| Medium Chain Triglycerides | 3.0 | 3.0 | 3.0 | 3.0 | 3.0 | 3.0 | — |
| Carbomer Homopolymer Type A (Carbopol 981), NF | 0.2 | 1.0 | — | — | — | 0.8 | 0.8 |
| Carbomer Copolymer Type B (Pemulen TR-1), NF | 0.8 | — | 1.0 | — | — | 0.2 | 0.2 |
| Carbomer Homopolymer Type B (Carbopol 974P), NF | — | — | — | 1.0 | — | — | — |
| Carbomer Homopolymer Type C (Carbopol 980), NF | — | — | — | — | 1.0 | — | — |
| Benzyl Alcohol, NF | | | | 0.9 | | | |
| Sodium Hydroxide, USP | | | | q.s. pH 5.5 ± 0.3 | | — | — |
| Trolamine, NF | — | — | — | — | — | q.s. pH 5.5 ± 0.3 | |
| Purified Water, USP | | | | Qsad 100 | | | |
| Initial Evaluation | Stable | Stable | Stable | Unstable | Stable | Stable | Stable |

Example 4

Exemplary Tretinoin Lotion

This example provides exemplary pharmaceutical composition of the present disclosure for delivery of tretinoin and that is formulated as a lotion, in comparison to the composition of a commercially available tretinoin gel composition (ATRALIN® (tretinoin) gel, 0.05%).

TABLE 4

Composition of Tretinoin Lotion and ATRALIN® Gel

| Ingredient | Function | Tretinoin lotion (%) | ATRALIN® gel (%) |
|---|---|---|---|
| Tretinoin | Anti-acne | 0.05 | 0.05 |
| Glycerin | Humectant | 9.63 | 9.63 |
| Soluble collagen | Moisturizing agent | 8.00 | 8.00 |
| Carbopol® 980 | Viscosity increasing agent | — | 0.90 |
| Carbomer homopolymer type A (Carbopol® 981) | Viscosity increasing agent | 0.70 | — |
| Carbomer copolymer type B (Pemulen® TR-1) | Emulsifier | 0.05 | — |
| Octoxynol -9 | Wetting agent | 0.12 | 0.12 |
| Sodium hyaluronate | Moisturizing agent | 0.011 | 0.011 |
| Methyl paraben | Antimicrobial preservative | 0.20 | 0.20 |
| Butylated Hydroxytoluene | Anti-oxidant | 0.21 | 0.21 |
| Benzyl alcohol | Antimicrobial preservative | 0.50 | 0.50 |
| Propyl paraben | Antimicrobial preservative | — | 0.03 |
| Mineral oil | Emollient | 2.00 | — |
| Trolamine | Neutralizing agent | pH 5.0-6.0 | pH 5.0-6.0 |
| Water | Carrier | qs 100 | qs 100 |

Manufacturing Process for Tretinoin Composition

A tretinoin composition as disclosed in Table 4 was manufactured according to the following manufacturing process:

A polymeric phase is made. In a suitable manufacturing vessel, purified water, Carbomer homopolymer type A (Carbopol 981), and Carbomer copolymer type B (Pemulen TR-1) are added and mixed until the contents are dispersed. Next, mineral oil is added and mixed.

Next, a moisturizing agent is prepared. In a separate suitable vessel, sodium hyaluronate and purified water are added and mixed until the sodium hyaluronate is dissolved. The contents of the vessel containing the sodium hyaluronate is added to the polymeric phase and the contents are mixed.

Next, a preservative phase is prepared. In a separate suitable vessel, glycerin is added and mixed while heating. Next, methylparaben and benzyl alcohol are added to the vessel and the contents are mixed until dissolved. The preservative phase is added to the vessel containing the polymeric phase, rinsed with glycerin, and mixed.

Next, an active phase is prepared. In a separate suitable vessel, purified water and glycerin are added, mixed, and blanketed with nitrogen. Next, under yellow lighting, butylated hydroxytoluene, octoxynol 9, and tretinoin are added to the vessel. The contents are mixed and then milled with recirculation. Under yellow lighting, the contents of the vessel containing the active phase are transferred to the vessel containing the polymeric phase, rinsed with purified water, and mixed. Next, under yellow lighting, soluble collagen is added to the vessel containing the polymeric phase and mixed.

Next, a neutralizing agent is prepared. In a separate suitable vessel, trolamine and purified water are added and mixed to form a solution having a pH of 5.0-6.0.

Next, under yellow lighting, the contents of the vessel containing the polymeric phase are transferred to a new vessel, rinsed with purified water, agitated, and recirculated under nitrogen. The pH of the composition is determined and the pH is adjusted with the neutralizing agent as necessary. The contents of the vessel are then transferred to a bulk storage container for filling secondary packaging.

Viscosity is determined in accordance with the current USP general chapter for viscosity determination. The test conditions include a temperature of 23°±2° C., spindle 27, and a speed of 12 rpm. Typical viscosity of compositions of the present invention are in the range of about 9000 to about 11000 cP. Depending on the amounts of various components, viscosity values can range from about 2500 cP to about 18000 cP.

Clinical Studies

A tretinoin lotion formulated as disclosed in Table 4 above was tested in comparison to a vehicle lotion and in comparison to a commercially available tretinoin gel, ATRALIN® (0.05% tretinoin). As described herein, the tretinoin lotion demonstrated an unexpectedly improved local tolerability (i.e., low irritation) profile as compared to ATRALIN® gel.

The safety and efficacy of once daily use of tretinoin lotion for the treatment of acne vulgaris were assessed in two prospective, multicenter, randomized, double-blind clinical trials in subjects 9 years and older with moderate to severe acne vulgaris. The trials compared 12 weeks of treatment with tretinoin lotion to the vehicle lotion. ATRALIN® gel and ATRALIN® gel vehicle were evaluated clinically in separate studies from the tretinoin lotion. The co-primary efficacy endpoints of absolute change in non-inflammatory lesion count, absolute change in inflammatory lesion count, and "treatment success" were assessed at Week 12. Treatment success was defined as at least a 2-grade improvement from Baseline in the Evaluators Global Severity Score (EGSS) score and an EGSS score equating to "clear" or "almost clear." Table 5 sets forth the EGSS scale that is used to assess the severity of the disease state. Table 6 lists the efficacy results for trials 1 and 2.

TABLE 5

Evaluator's Global Severity Score (EGSS)

| Score | Grade | Description |
| --- | --- | --- |
| 0 | Clear | Normal, clear skin with no evidence of acne |
| 1 | Almost Clear | Rare noninflammatory lesions present, with rare noninflamed papules (papules must be resolving and may be hyperpigmented, though not pink-red) |
| 2 | Mild | Some noninflammatory lesions are present, with few inflammatory lesions (papules/pustules only; no nodulocystic lesions) |
| 3 | Moderate | Noninflammatory lesions predominate, with multiple inflammatory lesions evident: several to many comedones and papules/pustules, and there may or may not be 1 nodulocystic lesion |
| 4 | Severe | Inflammatory lesions are more apparent, many comedones and papules/pustules, there may or may not be up to 2 nodulocystic lesions |

TABLE 6

Results of Phase 3 Trials in Subjects with Acne Vulgaris at Week 12

| | Tretinoin Lotion | Tretinoin Lotion Vehicle | ATRALIN® Gel | ATRALIN® Gel Vehicle |
| --- | --- | --- | --- | --- |
| Trial 1 | | | | |
| Evaluators Global Severity Score (EGSS) | | | | |
| Clear or Almost Clear and 2-Grade Reduction from Baseline | 16.5% | 6.9% | 21% | 12% |
| Non-Inflammatory Facial Lesions | | | | |
| Mean Absolute Reduction | 17.8 | 10.6 | 21.8 | 10.3 |
| Mean Percent Reduction | 47.5% | 27.3% | 43% | 21% |

TABLE 6-continued

Results of Phase 3 Trials in Subjects with Acne Vulgaris at Week 12

|  | Tretinoin Lotion | Tretinoin Lotion Vehicle | ATRALIN ® Gel | ATRALIN ® Gel Vehicle |
|---|---|---|---|---|
| Inflammatory Facial Lesions | | | | |
| Mean Absolute Reduction | 13.1 | 10.2 | 9.7 | 5.8 |
| Mean Percent Reduction | 50.9% | 40.4% | 41% | 26% |
| Trial 2 | | | | |
| EGSS | | | | |
| Clear or Almost Clear and 2-Grade Reduction from Baseline | 19.8% | 12.5% | 23% | 14% |
| Non-Inflammatory Facial Lesions | | | | |
| Mean Absolute Reduction | 21.9 | 13.9 | 18.7 | 10.8 |
| Mean Percent Reduction | 45.6% | 31.9% | 37% | 20% |
| Inflammatory Facial Lesions | | | | |
| Mean Absolute Reduction | 13.9 | 10.7 | 7.0 | 4.0 |
| Mean Percent Reduction | 53.4% | 41.5% | 30% | 17% |

Improvement in Local Tolerability

Increases in signs and symptoms of local tolerability with use of a retinoid in the instant invention is an unexpected outcome. As detailed below, it has been surprisingly found that formulating tretinoin as a lotion according to the methods disclosed herein resulted in a marked improvement in the tolerability profile of the tretinoin, as compared to the tolerability profile of tretinoin formulated as a gel.

Table 7 below summarizes the treatment emergent adverse events ("TEAEs") reported in each of the programs using data from pivotal phase 3 clinical studies as described above. The preferred terms are coded to the Medical Dictionary for Regulatory Activities (MedDRA) current at the time of each study.

TABLE 7

Comparison of Treatment Emergent Adverse Events from Tretinoin Lotion and ATRALIN ® Gel Clinical Studies

| | TEASs by MedDRA SOC and PT (Safety Population) | | | Overall Summary for AE's (Safety Subjects) | |
|---|---|---|---|---|---|
| System Organ Class (SOC) and Preferred Term (PT) | Tretinoin Lotion (N = 767) | Tretinoin Vehicle Lotion (N = 783) | MedDRA (SOC) | Atralin Gel (N = 674) | Atralin Gel Vehicle (N = 487) |
| General disorders and administration site conditions | 78 (10.2%) | 29 (3.7%) | Skin and subcutaneous tissue disorders | 208 (31%) | 25 (5%) |
| Application site dryness | 29 (3.8%) | 1 (0.1%) | Dry Skin | 109 (16%) | 8 (2%) |
| Application site pain | 25 (3.3%) | 3 (0.4%) | Pain of Skin | 7 (1%) | 0 |
| Application site erythema | 12 (1.6%) | 1 (0.1%) | Erythema | 47 (7%) | 1 (<1%) |
| Application site pruritus | 7 (0.9%) | 4 (0.5%) | Pruritus + Pruritus generalized | 12 (2%) | 3 (1%) |
| Application site irritation | 7 (0.9%) | 1 (0.1%) | Skin irritation | 3 (<1%) | 0 |
| Application site exfoliation | 6 (0.8%) | 3 (0.4%) | Skin exfoliation + skin desquamation | 28 (4%) | 2 (<1%) |
| Application site dermatitis | 3 (0.4%) | 1 (0.1%) | Dermatitis + D. exfolative + D. seborrheic | 39 (6%) | 4 (1%) |
| Application site rash | 3 (0.4%) | 0 | | | |
| Application site swelling | 2 (0.3%) | 0 | Face edema + skin swelling | 2 (<1%) | 0 |
| Application site ulcer | 2 (0.3%) | 0 | Ulcer | 0 | 0 |
| Application site burn | 1 (0.1%) | 0 | Skin burning sensation | 53 (8%) | 8 (2%) |
| Application site discoloration | 1 (0.1%) | 0 | Skin hypopigmentation | 1 (<1%) | 0 |
| Application site acne | 0 | 2 (0.3%) | | | |
| Application site urticarial | 0 | 1 (0.1%) | Urticaria | 1 (<1%) | 0 |
| Skin and subcutaneous tissue disorders | 5 (0.7%) | 6 (0.8%) | | | |
| Dermatitis contact | 2 (0.3%) | 1 (0.1%) | Dermatitis contact | 6 (1%) | 1 (1%) |
| Eczema | 1 (0.1%) | 1 (0.1%) | Eczema + Ecz nummular + Ecz weeping | 0 | 1 (<1%) |
| Pityriasis rosea | 1 (0.1%) | 0 | Pityriasis rosacea | 1 (<1%) | 0 |
| Acne | 0 | 1 (0.1%) | Acne | 3 (<1%) | 1 (<1%) |
| Rash | 0 | 1 (0.1%) | Rash + Rash generalized + Rash macular + Rash pruritic + Rash scaly | 21 (3%) | 1 (<1%) |

As shown in Table 7, tretinoin lotion demonstrated superior tolerability over ATRALIN® gel for several key signs and symptoms of local irritation listed below. Note that the comparisons are presented as reported percentages of adverse events ("AEs") for tretinoin lotion vs. ATRALIN® gel.

Dry skin (3.8% vs. 16%)
Burning (0.1% vs. 8%)
Erythema (1.6% vs. 7%)
Exfoliation (0.8% vs. 4%)

Thus, formulation of an active agent, tretinoin, in a composition comprising an oil-in-water emulsion comprising a liquid oil component, a cross-linked homopolymer based on acrylic acid (e.g., Carbopol® 981), a cross-linked copolymer of acrylic acid and acrylic acid esters (e.g., Pemulen® TR-1), and water yielded a topical composition exhibiting superior properties as compared to a gel formulation of the active agent.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, patent applications, or other documents cited herein are hereby incorporated by reference in their entirety for all purposes to the same extent as if each individual publication, patent, patent application, or other document was individually indicated to be incorporated by reference for all purposes.

What is claimed is:

1. A topical composition comprising:
   a liquid oil component;
   a cross-linked homopolymer based on acrylic acid as a first emulsifier; and
   water;
   wherein the composition does not comprise a cross-linked copolymer of acrylic acid and acrylic acid esters; and
   wherein the composition forms a stable oil-in-water emulsion.

2. The topical composition of claim 1, wherein the liquid oil component is present in an amount of about 30% or less by weight of the composition.

3. The topical composition of claim 2, wherein the liquid oil component is present in an amount of about 20% or less by weight of the composition.

4. The topical composition of claim 1, wherein the first emulsifer is present in an amount of about 0.01-5% by weight of the composition.

5. The topical composition of claim 4, wherein the first emulsifier is present in an amount of about 0.01-3% by weight of the composition.

6. The topical composition of claim 1, wherein the ratio of the amount of the liquid oil component to that of the first emulsifer is in the range of about 1:1 to about 28:1.

7. The topical composition of claim 6, wherein the ratio of the amount of the liquid oil component to that of the first emulsifer is in the range of about 1:1 to about 20:1.

8. The topical composition of claim 6, wherein the ratio of the amount of the liquid oil component to that of the first emulsifer is in the range of about 3:1 to about 10:1.

9. The topical composition of claim 1, wherein first emulsifer is a carbomer homopolymer type A and/or a carbomer homopolymer type C.

10. The topical composition of claim 1, wherein the liquid oil component comprises mineral oil, light mineral oil, a fatty alcohol, a monocarboxylic acid ester, a dicarboxylic acid ester, a medium chain triglyceride, a long chain triglyceride, or a combination thereof.

11. The topical composition of claim 1, wherein the composition further comprises a nonionic, anionic, or cationic surfactant in an amount up to about 0.5% by weight of the composition.

12. The topical composition of claim 1, further comprising an active agent.

13. A topical composition, wherein the composition comprises an oil-in-water emulsion, wherein the emulsion comprises:
    a liquid oil component, wherein the liquid oil component is in an amount of about 30% or less by weight of the composition;
    a cross-linked homopolymer based on acrylic acid in an amount of about 0.01-5% by weight of the composition; and
    water;
    wherein the composition does not comprise a cross-linked copolymer of acrylic acid and acrylic acid esters.

14. The topical composition of claim 13, wherein the polymer is a cross-linked homopolymer based on acrylic acid.

15. The topical composition of claim 13, further comprising an active agent.

* * * * *